United States Patent [19]

Manoh et al.

[11] Patent Number: 5,026,644
[45] Date of Patent: Jun. 25, 1991

[54] PROCESS FOR PREPARING A LIPID COMPOSITION HAVING A HIGH GAMMA-LINOLENIC ACID CONTENT

[75] Inventors: Yumiko Manoh; Akira Seto, both of Yokohama, Japan

[73] Assignee: The Nisshin Oil Mills, Ltd., Tokyo, Japan

[21] Appl. No.: 403,791

[22] Filed: Sep. 6, 1989

Related U.S. Application Data

[63] Continuation of Ser. No. 40,248, Apr. 20, 1987, which is a continuation of Ser. No. 681,197, Dec. 13, 1984, abandoned.

[30] Foreign Application Priority Data

Dec. 14, 1983 [JP] Japan ................................ 58-234295

[51] Int. Cl.$^5$ ................................................ C12P 7/64
[52] U.S. Cl. .................................................... 435/134
[58] Field of Search ........................................ 435/134

[56] References Cited

U.S. PATENT DOCUMENTS 4,871,666 10/1989 Seto ...................................... 435/134

OTHER PUBLICATIONS

Bekhtereva et al., Microbiology (Engl. Translation Mikrobiologiya), vol. 42(2); 1973; pp. 208–212.
Microbiology (Engl. Translation Mikrobiologiya), vol. 42(2), 1973; pp. 208–212; Bekhtereva et al.

*Primary Examiner*—Stanley J. Friedman
*Assistant Examiner*—Terry Wilson
*Attorney, Agent, or Firm*—Bacon & Thomas

[57] ABSTRACT

A lipid composition having a high γ-linolenic acid content is prepared by culturing mold fungi of the genus Cunninghamella in an aqueous nutrient culture medium having a relatively high concentration of a carbon source, and the lipid composition is recovered from the cultured mold fungi.

44 Claims, No Drawings

PROCESS FOR PREPARING A LIPID COMPOSITION HAVING A HIGH GAMMA-LINOLENIC ACID CONTENT

This application is a continuation of U.S. patent application Ser. No. 07/040,248 filed Apr. 20, 1987, now abandoned, which is a continuation of U.S. patent application Ser. No. 06/681,197 filed Dec. 13, 1984, now abandoned.

BACKGROUND OF THE INVENTION

1. Field of the Invention

The present invention relates to a process for preparing a lipid composition having a high γ-linolenic acid content and, more particularly, to a process for preparing such a composition from a specific living microorganism.

2. Description of the Prior Art 6,9,12- octadecatrienoic acid or γ-linolenic acid (to be referred to as GLA hereinafter) is a fatty acid synthesized in a living organism from linoleic acid. GLA is converted into prostaglandin $E_1$, $F_1$, $E_2$ or $F_2$ through bishomo-γ-linolenic acid. It has been found recently that the in vivo conversion reaction of linoleic acid into GLA is hindered by aging, alcohol drinking, and vitamin deficiency. An imbalance in prostaglandin due to a GLA deficiency is considered to be a factor causing allergic diseases, thrombosis, or cancer.

GLA which is therefore important to the health of living organisms is obtainable from plant seeds such as seeds of the evening primrose. However, GLA is contained in evening primrose seeds in small amounts and accounts for at most 10% by weight of the total fatty acid content. Furthermore, plant seed oil also contains about 70% by weight based on the total fatty acid content of linoleic acid. When GLA is obtained by refining a fatty acid mixture obtained from plant seed oil by solvent fractionation or the like, GLA cannot be easily separated from linoleic acid since the two components behave in a similar manner.

It has been proposed to obtain GLA from the lipids of microorganisms. See, for example, R. O. Mumma, Lipids, 6, 584 (1971); R. Shaw, Biochem. Biophys. Acta. 98, 230 (1965); and Suzuku et. al., Yukagaku, 30, 863, (1981). However, the GLA content of the GLA producing microorganisms mentioned in these articles is low and represents at most 10 to 20% of the total lipid content. Japanese Patent Publication (Kokoku) No. 58-22199 reports that when mold fungi of the genus Mortierella are cultured in a medium to which a hydrocarbon is added, the cultured fungi will have a GLA content of 20% or more based on the total fatty acid content. However, mold fungi of the genus Mortierella grow at slow rate and grow particularly slow at a low temperature which is most conducive for them to produce GLA. Therefore, the GLA productivity of these fungi is low.

The present invention is directed to a technique for producing GLA from cultured microorganisms.

SUMMARY OF THE INVENTION

It is, therefore, an object of the present invention to provide a novel process for preparing from cultured microorganisms a lipid composition containing a high concentration of GLA.

In order to achieve the above object of the present invention, there is provided a process for preparing a lipid composition having a high γ-linolenic acid content, comprising the steps of:

culturing mold fungi of the genus Cunninghamella in an aqueous nutrient culture medium containing a relatively high concentration of a carbon source; and recovering the lipid composition from the cultured mold fungi.

A fatty acid composition containing a high concentration of GLA can be obtained by saponifying the thus obtained lipid composition.

DETAILED DESCRIPTION OF THE PREFERRED EMBODIMENTS

In order to determine which strains satisfy the conditions of a high lipid content, a high GLA content in the lipid and a fast growth, the present inventors screened strains from a catalogue. As a result of this screening, it was found that Cunninghamella elegans (to be referred to as C. elegans hereinafter; accession numbers NRRL-1378, 1379, 1380 and 1381) best satisfied these requirements. As a result of further studies made on the basis of this finding, it was also found that mold fungi of the genus Cunninghamella other than C. elegans substantially satisfy the above conditions and that culturing of such mold fungi in a specific culture medium can yield a lipid composition having a high GLA content. The present invention has thus been established.

The mold fungi of the genus Cunninghamella to be used herein belong to mucorales of Zygomycetes. They have grayish white hypha and are aerobic. The appropriate temperature for growth is 25° to 30° C.

These fungi are all deposited in NRRL and are described in their catalogue. C. elegans is particularly preferable. However, Cunninghamella blackesleeana, accession number NRRL-1373 and Cunninghamella echinulate, accession number NRRL-1383 can also be used. It has been confirmed in the art that these mold fungi of the genus Cunninghamella do not produce a toxic substance such as aflatoxin.

These mold fungi can be generally cultured by static culture, shaking culture or aerated stirring culture using a liquid culture medium. A culture medium to be used is limited only in that it must contain carbon and nitrogen sources. However, a culture medium containing a relatively high concentration of a carbon source is preferably used.

An organic carbon source such as glucose or sodium acetate is preferable. Such a carbon source is contained, preferably, in the amount of 3 to 20% by weight based on the total weight of the culture medium. More preferably, the culture medium contains such a carbon source in the amount of 5 to 15% by weight.

A nitrogen source may be an organic nitrogen source such as yeast extract, malt extract, peptone, or urea; or an inorganic nitrogen source such as a nitrate or ammonium sulfate. Preferably, the nitrogen source is contained in the amount of 0.5 to 2% by weight based on the total weight of the culture medium.

As has been described earlier, the culture medium to be used herein is an aqueous liquid culture medium. This liquid culture medium can be prepared by dissolving the carbon and nitrogen sources in water. Preferably, the liquid culture medium is weakly acidic or neutral (pH 4.0 to 6.0). When vitamins such as vitamin B6 or biotin are added in the culture medium, growth of mold fungi is facilitated. It is preferred that vitamin B6 and biotin are added to the medium in the amounts of 0.1 to 0.5 mg % and 0.001 to 0.005 mg %, respectively. Other source elements may be contained in the medium. Such source elements include a phosphorus source (e.g., potassium dihydrogen phosphate), a sodium source (e.g., sodium chloride), a magnesium source (e.g., magnesium sulfate), an iron source (e.g., ferrous sulfate), a calcium source (e.g., calcium chloride), a copper source (e.g., cupric sulfate), a zinc source (e.g., zinc sulfate), or a manganese source (e.g., manganese chloride).

When mold fungi of the genus Cunninghamella are cultured, using a culture medium as described above, the mold fungi are generally inoculated in the amount of 0.5 to 5 grams per liter of the medium. Culturing is preferably performed within a temperature range of 15° to 30° C. The culture period is 4 to 15 days.

The mold fungi cultured in this manner are recovered by filtering and the lipid content is extracted from the recovered mold fungi. Since the lipid containing GLA is not secreted in the medium during culturing, the culture medium need not be recovered.

The lipids can be extracted by adding glass beads to the recovered wet mold fungi and homogenizing the mixture with an organic solvent such as hexane or alcohol so as to allow lipids in the fungi to be transferred into the solvent. The solvent phase containing the lipids is recovered by a means such as filtering, and the desired lipids are obtained by removing the solvent from the recovered solvent phase by reduced pressure distillation or the like. The amount of the solvent used is generally about 2 to 5 times by weight that of the wet fungi. Homogenization is preferably performed at a temperature of about 10° to 20° C.

Another method can be used to extract the lipids. According to this method, the recovered wet mold fungi are freeze-dried in a temperature range of −20° C. to −40° C. Thereafter, the mold fungi are brought into sufficient contact with an organic solvent such as a mixture of hexane and isopropanol, hexane and ethanol, or chloroform and methanol so as to allow the lipids to be transferred into the solvent. Preferably, the solvent is used in the amount about 4 to 10 times the weight of the fungi. The mold fungi are brought into contact with the solvent at a temperature of, preferably, 10° to 20° C. and for a time period of 1 to 3 hours. After the extraction, the solvent phase containing lipids is recovered by filtering, and the solvent is removed from the recovered solvent phase by reduced pressure distillation or the like.

A fatty acid composition which can be obtained by saponification of the lipids extracted from mold fungi of the genus Cunninghammela cultured in this manner contains 20% by weight or more of GLA. The fatty acid composition contains a relatively small amount of fatty acids such as linoleic acid which have physical properties similar to those of GLA. Therefore, the purification of GLA is relatively easy.

When the lipids extracted in this manner are saponified (subjected to hydrolysis), an acid (e.g., a mineral acid such as hydrochloric acid or sulphuric acid) or an alkali (e.g., sodium hydroxide or potassium hydroxide) is used in the amount of 0.25 to 0.50 parts by weight based on one part of the lipids, and saponification is performed in a suitable organic solvent (e.g., an alcohol such as methanol). The hydrolysis temperature is generally selected to be 70° to 80° C. and the hydrolysis time is selected to be 30 minutes to 2 hours. During hydrolysis, the lipids are decomposed and the fatty acids are liberated. After the unsaponified materials are extracted and removed by a nonpolar solvent such as petroleum ether and the residue is acidified, the fatty acids are extracted using an organic solvent such as petroleum ether. Extraction of the fatty acids is preferably performed within a temperature range of 10° to 20° C. After the extraction of the fatty acids, the solvent is distilled off to provide a desired fatty acid composition. As described above, this fatty acid composition contains GLA in an amount of 20% by weight or more. The fatty acid composition contains other fatty acid components such as palmitic acid, stearic acid, oleic acid, and linoleic acid.

The present invention will now be described by way of its Examples.

EXAMPLE 1

An aqueous organic nutrient culture medium having the composition shown in Table A below was prepared.

TABLE A

| (Culture Medium Composition) | |
|---|---|
| Yeast extract | 2 g/l |
| Malt extract | 3 g/l |
| Peptone | 3 g/l |
| Glucose | 50 g/l |
| Water | Balance to prepare 1 liter of composition |

0.2 grams of *C. elegans* (NRRL-1378) were inoculated in one liter of this medium and incubation was performed by shaking culture, which was done by horizontal turning at 100 rpm at 27° C. for 5 days. After culturing, the mixture was filtered to recover the fungi which were freeze-dried at −30° C. 2.5 grams of dried fungi were obtained per liter of the medium. The mold fungi were mixed with 20 grams of a solvent mixture of n-hexane and isopropanol in the ratio of 3:2 (Vol./Vol.) and the mixture was vigorously stirred at 10° C. The solvent phase was recovered by filtering and the solvent was distilled off by reduced pressure distillation. 0.4 grams of the lipids were thus obtained.

In order to perform saponification, a mixture of 2N NaOH and methanol was added to a portion of the lipids. The mixture was heated at 75° C. for 120 minutes in hot water bath. After the unsaponified materials were removed, the residue was acidified, and fatty acids were extracted with hexane. Then the solvent phase was recovered, and solvent was distilled off from the solvent phase to provide a fatty acid composition. The fatty acid composition was subjected to methyl esterification by a conventional method to analyze the fatty acid composition by gas chromatography. The analysis results are shown in Table B below.

TABLE B

| (Fatty Acid Composition) | | | | | |
|---|---|---|---|---|---|
| Fatty acid | $16:0^{(1)}$ | $18:0^{(2)}$ | $18:1^{(3)}$ | $18:2^{(4)}$ | $18:3\ (\gamma)^{(5)}$ |
| % by weight | 13.2 | 8.1 | 27.1 | 23.6 | 24.5 |

Note:
[1] Palmitic acid
[2] Stearic acid
[3] Oleic acid
[4] Linoleic acid
[5] GLA

EXAMPLE 2

An aqueous culture medium as shown in Table C below was prepared.

TABLE C

| (Culture Medium Composition) | |
| --- | --- |
| Yeast extract | 2 g/l |
| Ammonium sulfate | 1 g/l |
| Glucose | 70 g/l |
| Vitamin B6 | 2 mg/l |
| Biotin | 0.02 mg/l |
| Water | Balance to prepare 1 liter of composition |

1.0 gram of the *C. elegans* (NRRL-1378) was inoculated in one liter of this culture medium and incubation was performed by shaking culture at 23° C. and 100 rpm for 6 days. After culturing, the mixture was processed in the same manner as in Example 1 to yield 3.2 grams of freeze-dried fungi. The fungi were extracted in the same manner as in Example 1 to yield 0.55 grams of lipids. The fatty acid composition in the lipids was analyzed following the procedures of Example 1, and the obtained results are shown in Table D below.

TABLE D

| (Fatty Acid Composition) | | | | | |
| --- | --- | --- | --- | --- | --- |
| Fatty acid | 16:0 | 18:0 | 18:1 | 18:2 | 18:3 ($\gamma$) |
| % by weight | 12.0 | 8.5 | 23.1 | 28.0 | 28.5 |

EXAMPLE 3

An aqueous culture medium having the composition in Table E below was prepared.

TABLE E

| (Culture medium compostion) | | | |
| --- | --- | --- | --- |
| Glucose | 150 g/l | Ferrous sulfate.7H$_2$O | 20 mg/l |
| Yeast extract | 1 g/l | Calcium chloride | 20 mg/l |
| Malt extract | 1 g/l | Cupric sulfate.5H$_2$O | 0.5 mg/l |
| Urea | 5 g/l | Zinc sulfate.7H$_2$O | 3 mg/l |
| Ammonium sulfate | 5 g/l | Manganese chloride.4H$_2$O | 3 mg/l |
| Potassium dihydrogen phosphate | 5 g/l | Vitamin B6 | 5 mg/l |
| Magnesium sulfate | 1 g/l | Biotin | 0.05 mg/l |
| Sodium chloride | 0.3 g/l | Water (Balance to prepare 1 liter of composition) | |

Thirty liters of this culture medium were charged in a jar fermentor and sterilized at a temperature of 120° C. and at a pressure of 1.5 kg/cm$^2$. Thereafter, 30 grams of *C. elegans* (NRRL-1378) were inoculated in the medium and air-blowing stirring culture was performed at 28° C. for 5 days. During culturing, 2N NaOH aqueous solution was added to maintain the pH of the medium at 4.0 or higher.

After culturing, the medium was processed in the same manner as in Example 1 to yield 1480 grams of the freeze-dried fungi. The fungi were extracted as in Example 1 to yield 520 grams of lipids.

The thus obtained lipids were saponified under the same conditions as those in Example 1 to provide 400 grams of fatty acids. The fatty acids had a composition as shown in Table F below.

TABLE F

| (Fatty Acid Composition) | | | | | |
| --- | --- | --- | --- | --- | --- |
| Fatty acid | 16:0 | 18:0 | 18:1 | 18:2 | 18:3 ($\gamma$) |
| % by weight | 11.0 | 7.6 | 24.5 | 28.9 | 26.3 |

According to the present invention, a lipid composition having a high GLA content can be prepared with simple procedures. Since an organic carbon source which is guaranteed to be safe such as glucose can be used, a lipid composition obtained is safe as compared to a case wherein hydrocarbon is used as a carbon source. Furthermore, as described above, mold fungi of the Cunninghamella genus used in the present invention do not produce any toxic substance.

Further, the GLA contained in the fatty acid composition can be further purified by the urea adduct process. For example, a mixture of one part by weight of fatty acid composition, 2 parts by weight of urea and 10 parts by weight of methanol is prepared and heated at about 60° C. The solution is allowed to stand at about 4° C. overnight. The thus treated solution is filtered to remove undissolved material including saturated and mono-unsaturated fatty acids such as palmitic, stearic and oleic acids. The filtrate contains highly unsaturated fatty acids such as linoleic acid and GLA. The evaporation of the solvent from the filtrate gives a fatty acid composition containing GLA in an amount of about 40% by weight.

The fatty acid composition obtained by the urea adduct process may be subjected to column chromatography in order to obtain a more purified GLA after the ethyl esterification. The ethyl esterification can be performed by heating a mixture of fatty acid composition (1 g), conc. sulfuric acid (0.2 g) and ethanol (10 ml) to 80° C. for 2 hrs. The fatty acid ethyl esters are extracted with petroleum ether. For the purification, a silica gel column is saturated with a first solvent mixture of hexane and ether at a ratio of 400/1 (vol./vol.). The ethyl esterified fatty acid composition is charged in the column in an amount of about 5% by weight based on the total weight of the silica gel. Then the first solvent mixture is passed through the column. When the GLA ethyl ester begins to elute, the solvent is changed to a second solvent mixture of hexane and ether at a ratio of 8/2 (vol./vol.). The thus obtained GLA ethyl ester fraction contains 80 to 95% by weight of GLA ethyl ester.

What is claimed is:

1. A process for preparing a lipid composition having a high $\gamma$-linolenic acid content of at least 20%, comprising:
   culturing mold fungi of the genus Cunninghamella in an aqueous nutrient culture medium having a relatively high concentration of carbon source of 3-20% by weight, said carbon source being an organic source of carbon assimilable by the fungi and capable of producing fatty acids containing at least 20% $\gamma$-linolenic acid when assimulated by the fungi in the nutrient medium; said culturing being performed under weakly acidic or neutral conditions; and
   recovering the lipid composition from the cultured mold fungi, said lipid composition containing at least 20% $\gamma$-linolenic acid.

2. A process according to claim 1, wherein the culture medium contains 3 to 20% by weight of the carbon source based on a total weight thereof.

3. A process according to claim 2, wherein the carbon source is glucose or sodium acetate.

4. A process according to claim 2, wherein the culturing step is performed at a temperature of 15° to 30° C. and with a weakly acidic or neutral culture medium.

5. A process according to claim 4, wherein the culturing step is performed by shaking culture.

6. A process according to claim 4, wherein the culturing step is performed by air-blowing stirring culture.

7. A process according to claim 1, wherein the recovering step is performed by extraction using an organic solvent.

8. A process according to claim 1, wherein the mold fungi are *Cunninghamella elegans*.

9. A process according to claim 1, wherein the mold fungi are *Cunninghamella blakesleegna*.

10. A process according to claim 1, wherein the mold fungi are *Cunninghamella echinulate*.

11. A process for preparing a fatty acid composition containing at least 20% γ-linolenic acid comprising:
    culturing mold fungi of the Cunninghamella genus in an aqueous nutrient culture medium containing a relatively high concentration of a carbon source of 3-20% by weight, said carbon source being an organic source of carbon assimilable by the fungi and capable of producing fatty acids containing at least 20% γ-linolenic acid when assimilated by the fungi in the nutrient medium; said culturing being performed under weakly acidic or neutral conditions;
    recovering the lipid composition from the cultured mold fungi, said lipid composition containing at least 20% γ-linolenic acid;
    saponifying the recovered lipid composition to liberate a fatty acid composition containing at least 20% γ-linolenic acid; and
    recovering the fatty acid composition.

12. A process according to claim 11, wherein the culture medium contains 3 to 20% by weight of the carbon source based on a total weight thereof.

13. A process according to claim 12, wherein the carbon source is glucose or sodium acetate.

14. A process according to claim 12, wherein the culturing step is performed at a temperature of 15° to 30° C. and with a weakly acidic or neutral culture medium.

15. A process according to claim 11, wherein the recovering step is performed by extraction using an organic solvent.

16. A process according to claim 11, wherein the mold fungi are *Cunninghamella elegans*.

17. A process according to claim 11, wherein the mold fungi are *Cunninghamella blakesleeana*.

18. A process according to claim 11, wherein the mold fungi are *Cunninghamella echinulate*.

19. A process according to claims 1 or 11, wherein said culture medium contains 0.5% to 2.0% by weight of a nitrogen source.

20. A process according to claim 19, wherein said nitrogen source is an organic nitrogen source.

21. A process according to claim 20, wherein said organic nitrogen source is selected from the group consisting of yeast extract, malt extract, peptone and urea.

22. A process according to claim 20, wherein said nitrogen source is an inorganic nitrogen source.

23. A process according to claim 22, wherein said inorganic nitrogen source is a nitrate or ammonium sulfate.

24. A process according to claims 1 or 11, wherein said culture medium contains 0.1 mg % to 0.5 mg % of biotin.

25. A process according to claims 1 or 11, wherein said culture medium contains 0.001 mg % to 0.005 mg % of biotin.

26. A process according to claims 1 or 11, wherein said culturing step is effected for 4 to 15 days.

27. A process for preparing a lipid composition having a high γ-linolenic acid content of at least 20% comprising: culturing mold fungi of the genus Cunninghamella in an aqueous nutrient culture medium having a carbon source selected from the group consisting of glucose and sodium acetate; and recovering the lipid composition from the cultured mold fungi, said lipid composition containing at least 20% γ-linolenic acid.

28. A process for preparing a fatty acid composition containing at least 20% γ-linolenic acid comprising: culturing mold fungi of the Cunninghamella genus in an aqueous nutrient culture medium containing a carbon source selected from the group consisting of glucose and sodium acetate; recovering the lipid composition form the cultured mold fungi, said lipid composition containing at least 20% γ-linolenic acid; saponifying the recovered lipid composition to liberate a fatty acid composition containing at least 20% γ-linolenic acid; and recovering the fatty acid composition.

29. The process of claims 27 or 28 wherein the culture medium contains 3-20% by weight of the carbon source based on the total weight thereof.

30. The process of claim 29 wherein the culturing step is performed at a temperature of 15°-30° C. and with a weakly acidic or neutral culture medium.

31. The process of claim 30 wherein the culturing step is performed by shaking culture.

32. The process of claim 30 wherein the culturing step is performed by air-blowing stirring culture.

33. The process of claims 27 or 28 wherein the recovering step is performed by extraction using an organic solvent.

34. The process of claims 27 or 28 wherein the mold fungi are *Cunninghamella elegans*.

35. The process of claims 27 or 28 wherein the mold fungi are *Cunninghamella bladesleeana*.

36. The process of claims 27 or 28 wherein the mold fungi are *Cunninghamella echinulate*.

37. The process of claims 27 or 28 wherein the culture medium contains 0.5% to 2.0% by weight of a nitrogen source.

38. The process of claim 37 wherein said nitrogen source is an organic nitrogen source.

39. The process of claim 38 wherein said organic nitrogen source is selected from the group consisting of yeast extract, malt extract, peptone and urea.

40. The process of claim 38 wherein said nitrogen source is an inorganic nitrogen source.

41. The process of claim 40 wherein said inorganic nitrogen source is a nitrate or ammonium sulfate.

42. The process of claims 27 or 28 wherein said culture medium contains 0.1 mg % to 0.5 mg % of biotin.

43. The process of claims 27 or 28 wherein said culture medium contains 0.001 mg % to 0.005 mg % of biotin.

44. The process of claims 27 or 28 wherein said culturing step is effected for four to fifteen days.

* * * * *